(12) United States Patent
Holick et al.

(10) Patent No.: US 7,217,696 B2
(45) Date of Patent: May 15, 2007

(54) GLYCURONAMIDES, GLYCOSIDES AND ORTHOESTER GLYCOSIDES OF FLUOXETINE, ANALOGS AND USES THEREOF

(75) Inventors: Michael F Holick, Sudbury, MA (US); Halasya Ramanathan, Mysore, IN (US)

(73) Assignee: A & D Bioscience, Inc., Sudbury, MA (US)

( * ) Notice: Subject to any disclaimer, the term of this patent is extended or adjusted under 35 U.S.C. 154(b) by 0 days.

(21) Appl. No.: 10/506,012

(22) PCT Filed: Feb. 27, 2003

(86) PCT No.: PCT/US03/06061

§ 371 (c)(1), (2), (4) Date: Aug. 30, 2004

(87) PCT Pub. No.: WO03/073988

PCT Pub. Date: Sep. 12, 2003

(65) Prior Publication Data

US 2005/0130908 A1    Jun. 16, 2005

Related U.S. Application Data

(60) Provisional application No. 60/359,887, filed on Feb. 28, 2002.

(51) Int. Cl.
 *A61K 31/70* (2006.01)
 *A61K 31/7024* (2006.01)
 *A61K 31/7028* (2006.01)

(52) U.S. Cl. .................... 514/23; 514/25; 514/646; 536/1.11; 536/18.7; 536/115

(58) Field of Classification Search ............ 514/23, 514/62, 42, 25, 646; 536/1.11, 52.2, 18.7, 536/115
See application file for complete search history.

(56) References Cited

U.S. PATENT DOCUMENTS

| | | |
|---|---|---|
| 4,261,974 A | 4/1981 | Buckler et al. |
| 4,292,425 A | 9/1981 | Buckler et al. |
| 4,595,695 A | 6/1986 | Ladkani et al. |
| 4,599,418 A | 7/1986 | Irikura et al. |
| 4,751,219 A | 6/1988 | Kempen |
| 4,774,230 A | 9/1988 | Tuttle et al. |
| 4,855,463 A | 8/1989 | Barua et al. |
| 4,894,476 A | 1/1990 | Butler et al. |
| 4,897,382 A | 1/1990 | della Valle et al. |
| 4,939,174 A | 7/1990 | Shashoua |
| 5,051,448 A | 9/1991 | Shashoua |
| 5,114,976 A * | 5/1992 | Norden ............ 514/646 |
| 5,162,573 A | 11/1992 | Chiesi et al. |
| 5,179,093 A | 1/1993 | Afonso et al. |
| 5,340,803 A | 8/1994 | Rubin |
| 5,412,083 A | 5/1995 | Giese et al. |
| 5,432,260 A | 7/1995 | Stahl |
| 5,436,253 A | 7/1995 | Rinaldi et al. |
| 5,436,325 A | 7/1995 | Johnson et al. |
| 5,440,023 A | 8/1995 | Cheng et al. |
| 5,466,681 A | 11/1995 | Krivan et al. |
| 5,506,224 A | 4/1996 | della Valle et al. |
| 5,508,392 A | 4/1996 | Holick |
| 5,518,738 A | 5/1996 | Eickhoff et al. |
| 5,559,235 A | 9/1996 | Luzzio et al. |
| 5,561,119 A | 10/1996 | Jacquesy et al. |
| 5,599,953 A | 2/1997 | Curley, Jr. et al. |
| 5,633,357 A | 5/1997 | Tius et al. |
| 5,677,286 A | 10/1997 | Shull et al. |
| 5,679,667 A | 10/1997 | Della Valle et al. |
| 5,707,605 A | 1/1998 | Meade et al. |
| 5,707,663 A | 1/1998 | Ayer et al. |
| 5,760,072 A | 6/1998 | de Bont et al. |
| 5,808,111 A | 9/1998 | Curley, Jr. |
| 5,827,819 A | 10/1998 | Yatvin et al. |
| 5,977,326 A | 11/1999 | Scheinmann et al. |
| 5,994,392 A | 11/1999 | Shashoua |
| 6,024,977 A | 2/2000 | Yatvin et al. |
| 6,043,367 A | 3/2000 | Roffler et al. |
| 6,074,625 A | 6/2000 | Hawthorne et al. |
| 6,107,499 A | 8/2000 | Shashoua |
| 6,166,089 A | 12/2000 | Kozak |
| 6,167,313 A | 12/2000 | Gray et al. |
| 6,207,700 B1 | 3/2001 | Kalgutkar et al. |
| 6,214,345 B1 | 4/2001 | Firestone et al. |

(Continued)

FOREIGN PATENT DOCUMENTS

GB    1029222    5/1966

(Continued)

OTHER PUBLICATIONS

Lemberger et al. (Journal of Clinical Psychiatry (1985), vol. 46:3 (Sec. 2), pp. 14-19.*

(Continued)

*Primary Examiner*—Shaojia Anna Jiang
*Assistant Examiner*—Michael C. Henry
(74) *Attorney, Agent, or Firm*—Sterne, Kessler, Goldstein & Fox P.L.L.C.

(57) ABSTRACT

Disclosed are glycosides, orthoester glycosides and glycuronamides of fluoxetine and analogs thereof to treat conditions and diseases such as depression.

10 Claims, No Drawings

U.S. PATENT DOCUMENTS

| | | | |
|---|---|---|---|
| 6,218,519 B1 | 4/2001 | Kenten et al. | |
| 6,277,818 B1 | 8/2001 | Mazar et al. | |
| 6,287,598 B1 | 9/2001 | Ayer et al. | |
| 6,313,106 B1 | 11/2001 | Kozak | |
| 6,316,027 B1 | 11/2001 | Johnson et al. | |
| 6,339,060 B1 | 1/2002 | Yatvin et al. | |
| 6,548,484 B1 | 4/2003 | Christian | |
| 7,001,888 B2 | 2/2006 | Tidmarsh et al. | |
| 2001/0041676 A1 | 11/2001 | Holick et al. | |
| 2002/0002140 A1 | 1/2002 | Holick et al. | |
| 2003/0216328 A1 | 11/2003 | Holick et al. | |
| 2004/0087559 A1 | 5/2004 | Schwartz et al. | |
| 2005/0107310 A1 | 5/2005 | Holick et al. | |
| 2005/0153928 A1 | 7/2005 | Holick et al. | |
| 2005/0215487 A1 | 9/2005 | Holick et al. | |
| 2005/0233949 A1 | 10/2005 | Holick et al. | |
| 2005/0255038 A1 | 11/2005 | Holick et al. | |

FOREIGN PATENT DOCUMENTS

| | | |
|---|---|---|
| WO | WO 92/18005 | 10/1992 |
| WO | WO 94/14411 | 7/1994 |
| WO | WO 96/03995 | 2/1996 |

OTHER PUBLICATIONS

Ali, S.A. et al., "Improving the Tumor Retention of Radioiodinated Antibody: Aryl Carbohydrate Adducts," *Canc. Res.* (*Suppl.*) 50:783S-788S, American Association for Cancer Research (1990).

Database STN Easy, Accession No. 2001:136552, Haubner et al. (Feb. 2001).

Murakami, K. et al., "Excretion of New Quinolones and their Glucuronide Conjugates into Human Bile," *Drugs 49* (*Suppl. 2*):331-332, Adis International Limited (1995).

Strobel, J.L. et al., "$^{125}$I-Glycoconjugate Labels for Identifying Sites of Protein Catabolism *in Vivo*: Effect of Structure and Chemistry of Coupling to Protein on Label Entrapment in Cells after Protein Degradation," *Arch. Biochem. And Biophys. 240*:635-645, Academic Press, Inc. (1985).

Esmond, R.W., Applicants' Amendents to the Claims for U.S. Appl. No. 10/512,848, 3 pages, "Amendment and Reply Under 37 C.F.R. § 1.111" (filed Mar. 2, 2006).

Fernández, C. et al., "Synthesis and biological studies of glycosyl dopamine derivatives as potential antiparkinsonian agents," *Carbohydrate Research 327*:353-365, Elsevier Science Ltd. (2000).

Maryanoff, B.E. et al, "Anticonvulsant O-Alkyl Sulfamates. 2,3,4,5-Bis-O-(1-methylethylidene)-β-D-fructopyranose Sulfamate and Related Compounds," *J. Med. Chem. 30*:880-887, American Chemical Society (1987).

Maryanoff, B.E. et al., "Structure-Activity Studies on Anticonvulsant Sugar Sulfamates Related to Topiramate. Enhanced Potency with Cyclic Sulfate Derivatives," *J. Med. Chem. 41*:1315-1343, American Chemical Society (1998).

Remington's Pharmaceutical Sciences, Osol, A., et al., eds., 16$^{th}$ edition, Chapter 36, pp. 677-678, Philadelphia College of Pharmacy and Science (1980).

Rowley, M. et al., "Effect of Plasma Protein Binding on in Vivo Activity and Brain Penetration of Glycine/NMDA Receptor Antagonists," *J. Med. Chem. 40*:4053-4068, American Chemical Society (1997).

Office Action for U.S. Appl. No. 10/512,848, Holick, M.F., et al., filed Oct. 29, 2004, mailed Dec. 15, 2005.

\* cited by examiner

GLYCURONAMIDES, GLYCOSIDES AND ORTHOESTER GLYCOSIDES OF FLUOXETINE, ANALOGS AND USES THEREOF

BACKGROUND OF THE INVENTION

1. Field of the Invention

The present invention relates to glycuronamides, glycosides and orthoester glycosides of fluoxetine and analogs and their use in therapy.

2. Related Art

Fluoxetine hydrochloride is a selective serotonin reuptake inhibitor and is sold as an antidepressant and for the treatment of eating disorders. Fluoxetine hydrochloride is also reported to be useful for the treatment of obsessive-compulsive disorder, bulimia, pain, obsessive-compulsive personality disorder, post-traumatic stress disorder, hypertension, atherosclerosis, anxiety, anorexia nervosa, panic, social phobia, stuttering, sleep disorders, chronic fatigue, Alzheimer's disease, alcohol abuse, appetite disorders, weight loss, agoraphobia, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of antidepressants, aggressive/intermittent explosive disorder, compulsive gambling, compulsive spending, compulsive sex, psychoactive substance use disorder, schizophrenia, premature ejaculation, or psychiatric symptoms selected from the group consisting of stress, worry, anger, rejection sensitivity, and lack of mental or physical energy without an increase in nausea. See U.S. Pat. Nos. 4,314,018, 4,626,549, 5,985,322 and 5,910,319.

Wirth, D.D. et al., *J. Pharm. Sci.* 87:31–39 (1998), discloses that generic formulations of fluoxetine hydrochloride comprise lactose and are inherently less stable than formulations containing starch due to the Maillard reaction between the fluoxetine and lactose. N-formylfluoxetine was identified as the major product.

SUMMARY OF THE INVENTION

The present invention relates to a pro-drug approach to fluoxetine therapy that provides better bioavailability. The pro-drug is in the form of glycosides, orthoester glycosides, glycuronamides and glycuronides of fluoxetine and analogs thereof. The secondary amino group in fluoxetine may be glycosylated cleanly to give one major isomer. In addition, the amino group may be glycuronamidated to give a glyouronamide. When administered, glycosidase and amidase enzymes in the biological medium of human body cleave the glycoside/orthoester glycoside/glycuronamide, thus liberating the free drug. Thus, the free drug is bioavailable in a controlled fashion as determined by the rate of deglycosylation/deamidation.

Fluoxetine is a serotonin reuptake inhibitor that acts on the central nervous system. Thus, fluoxetine and analog glycosides/ortho ester glycosides can be used for the treatment of depression, eating disorders, obsessive-compulsive disorder, bulimia, pain, obsessive-compulsive personality disorder, post-traumatic stress disorder, hypertension, atherosclerosis, anxiety, anorexia nervosa, panic, social phobia, stuttering, sleep disorders, chronic fatigue, Alzheimer's disease, alcohol abuse, appetite disorders, weight loss, agoraphobia, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of antidepressants, aggressive/intermittent explosive disorder, compulsive gambling, compulsive spending, compulsive sex, psychoactive substance use disorder, schizophrenia, premature ejaculation, or psychiatric symptoms selected from the group consisting of stress, worry, anger, rejection sensitivity, and lack of mental or physical energy without an increase in nausea.

In a first aspect, the present invention provides a composition for the treatment of a condition treatable by the administration of fluoxetine or analog thereof, characterized in that the fluoxetine or analog thereof is a derivative in the form of a glycuronamide, glycoside or orthoester glycoside or salt or ester of the derivative.

The present invention also relates to compounds of the Formula (I):

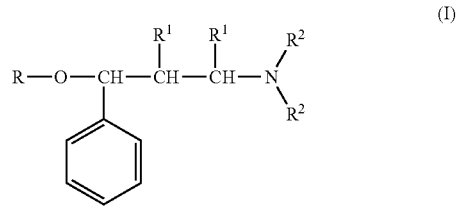

wherein each $R^1$ is independently hydrogen or methyl;

wherein one $R^2$ is methyl and the other $R^2$ is a glycuronamide, glycoside or ortho ester glycoside;

wherein R is naphthyl or

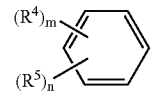

wherein $R^4$ and $R^5$ are halo, trifluoromethyl, $C_1$–$C_4$ alkyl, $C_1$–$C_3$ alkoxy or $C_3$–$C_4$ alkenyl; and wherein n and m are 0, 1 or 2; and acid addition salts thereof formed with pharmaceutically-acceptable acids.

Preferably, one $R_2$ is a straight or branched chain glycosidic residue containing 1–20 glycosidic units per residue, or is an orthoester glycoside moiety of the Formula (II):

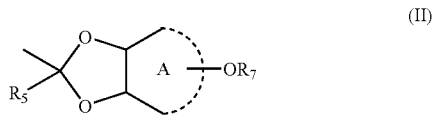

wherein A represents a glycofuranosyl or glycopyranosyl ring;

$R^6$ is hydrogen;

$R^7$ is hydrogen or a straight or branched chain glycosidic residue containing 1–20 glycosidic units per residue.

In a preferred embodiment, the compound has Formula (III or IV):

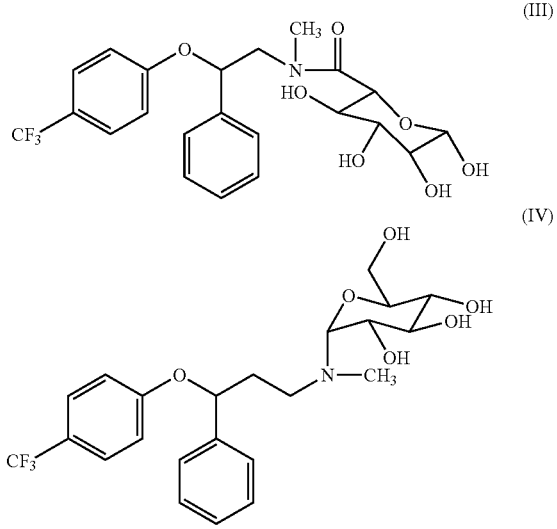

or a salt thereof.

The invention also relates to a method for the treatment or amelioration of any condition treatable with fluoxetine hydrochloride, comprising administering to an animal in need thereof, an effective amount of a compound having the Formula (I), or a pharmaceutically acceptable salt thereof.

The invention also relates to a method of preparing a compound of Formula (I) which comprises condensing a saccharide with fluoxetine or analog thereof in solvent, and isolating the glycoside.

The invention also relates to a method of preparing a compound of Formula (I) which comprises condensing a protected glycuronolactone with fluoxetine or analog thereof in a solvent and removing the protecting groups.

DETAILED DESCRIPTION OF THE INVENTION

Where the derivative is a glycoside, then it is preferred that it contain 1–20 glycosidic units.

It is preferred that compounds of the present invention have less than 10 and, more preferably, 3 or less glycosidic units. Specific examples are those containing 1 or 2 glycosidic units in the glycoside residue, such as glucose and sucrose, with one being most preferred.

By glycosidic units are meant glycopyranosyl or glycofuranosyl, as well as their sulfates, amino sugar and/or deoxy derivatives. The configuration of each unit may be D or L, although D is generally preferred. The residues may be homopolymers, random or alternating polymers, or block copolymers of these monomers.

The glycosidic units have free hydroxy groups, or the hydroxy groups may be acylated, e.g. with a group $R_4$—(C=O)—, wherein $R_4$ is hydrogen, $C_{1-6}$ alkyl, $C_{6-10}$ substituted or unsubstituted aryl or $C_{7-16}$ aralkyl. Preferably, the acyl groups are acetyl or propionyl. Other preferred $R_4$ groups are phenyl, nitrophenyl, halophenyl, lower alkyl substituted phenyl, lower alkoxy substituted phenyl and the like or benzyl, lower alkoxy substituted benzyl and the like.

The glycopyranose or glycofuranose ring or amino derivative thereof may be fully or partially acylated or completely deacylated. The completely or partially acylated glycoside is useful as a defined intermediate for the synthesis of the deacylated material. Useful protecting groups include, but are not limited to, acetyl, benzoyl, nicotinoyl, benzyl, methyl and phenyl.

Among the possible glycopyranosyl structures are glucose, mannose, galactose, gulose, allose, altrose, idose, or talose. Among the furanosyl structures, the preferred ones are derived from fructose, ribose, arabinose or xylose. Among preferred diglycosides are sucrose, cellobiose, maltose, lactose, trehalose, gentiobiose, and melibiose. Among the triglycosides, the preferred ones may be raffinose or gentianose.

Where there are linked glycosidic units, i.e., there is a di or polyglycosidic residue, the individual glycosidic rings may be bonded by 1-1, 1-2, 1-3, 1-4, 1-5 or 1-6 bonds, most preferably 1-2, 1-4 and 1-6. The linkages between individual glycosidic rings may be α or β.

Glycuronamides include glucuronamides and galacturonamides.

In Formula (I), when R is naphthyl, it can be either alpha-naphthyl or beta-naphthyl. $R^4$ and $R^5$ when they are halo, $C_1$–$C_4$ alkyl, $C_1$–$C_3$ alkyloxy or $C_3$–$C_4$ alkenyl represent, illustratively, the following atoms or groups: fluoro, chloro, bromo, iodo, methyl, ethyl, isopropyl, n-propyl, n-butyl, isobutyl, sec.-butyl, t-butyl, methoxy, ethoxy, n-propoxy, isopropoxy, allyl, methallyl, crotyl and the like. R thus can represent o, m and p-trifluoromethylphenyl, o, m and p-chlorophenyl, o, m and p-bromophenyl, o, m and p-fluorophenyl, o, m an p-toyl, xylyl including all position isomers, o, m and p-anisyl, o, m and p-allylphenyl, o, m and p-methylallylphenyl, o, m and p-phenetolyl(ethoxyphenyl), 2,4-dichlorophenyl, 3,5-difluorophenyl, 2-methoxy-4-chlorophenyl, 2-methyl-4-chlorophenyl, 2-ethyl-4-bromophenyl, 2,4,6-triethylphenyl, 2-fluorotrifluoromethylphenyl, 2,4,6-trichlorophenyl, 2,4,5-trichlorophenyl, and the like.

Especially preferred compounds include the glycosides, e.g. glucosides, and glucuronides of any one of the following compounds:

N-methyl 3-(4'-trifluoromethylphenoxy)-3-phenylpropylamine,
3-(p-isopropoxyphenoxy)-3-phenylpropylamine,
N-methyl 3-(3',4'-dimethoxyphenoxy)-3-phenylpropylamine,
N-methyl 3-(α-naphthoxy)-3-phenylpropylamine,
N-methyl 3-(β-naphthoxy)-3-phenyl-1-methylpropylamine,
3-(2'-methyl-4',5'-dichlorophenoxy)-3-phenylpropylamine,
3-(p-t-butylphenoxy)-3-phenylpropylamine,
N-methyl-3-(2'-chloro-p-tolyloxy)-3-phenyl-1-methylpropylamine,
3-(2',4'-dichlorophenoxy)-3-phenyl-2-methylpropylamine,
N-methyl-3-(m-anisyloxy)-3-phenyl-1-methylpropylamine,
N-methyl 3-(p-tolyloxy)-3-phenylpropylamine,
N-methyl 3-(2',4'-difluorophenoxy)-3-phenylpropylamine,
3-(o-ethylphenoxy)-3-phenylpropylamine,
N-methyl 3-(2'-chloro-4'-isopropylphenoxy)-3-phenyl-2-methylpropylamine,
N-methyl 3-(2'-alkyl-4'-fluorophenoxy)-3-phenylpropylamine,
N-methyl 3-(o-isopropoxyphenoxy)-3-phenyl-propylamine,
N-methyl 3-(o-bromophenoxy)-3-phenyl-propylanine,
N-methyl 3-(p-iodophenoxy)-3-phenyl-propylamine,
N-methyl 3-(3-n-propylphenoxy)-3-phenyl-propylamine,
and the pharmaceutically acceptable salts thereof.

Salts of the compounds of the invention include any pharmaceutically acceptable salts include the acid addition salts with e.g. hydrogen chloride, sulfuric acid, phosphoric acid, acetic acid, malic acid, carbonic acid and the like.

Esters of the compounds of the invention include esters of any free hydroxy groups on the glycosides, orthoester glycosides and glycuronamides. Such esters include the group R₄—(C=O)—, wherein R₄ is as defined above.

The water soluble glycosidic derivatives of the aforementioned fluoxetine and analogs thereof may be obtained according to the general methods disclosed U.S. Pat. No. 4,410,515, the contents of which are fully incorporated by reference herein.

The invention also relates to a method of preparing a compound of Formula (I) which comprises condensing a saccharide with fluoxetine or analog thereof in solvent such as dimethylformamide or lower alcohol such as methanol and ethanol, and isolating the glycoside.

The invention also relates to a method of preparing a compound of Formula (I) which comprises condensing a protected glycuronolactone with fluoxetine or analog thereof in a solvent and removing the protecting groups. Glycuronamides may be prepared by acylation of the fluoxetine amino group with, e.g. a hydroxy group protected active ester form of the glycuronic acid like 1-Naphthyl β-D-glucuronic acid or Naphthol-AS-BI-β-D-glucuronic acid which are available commercially or anyother anomerically protected glucuronic acid. The amide bond between the anomerically protected glycuronic acid can be obtained by reaction with DMT-MM (4-(4,6-dimethoxy-1,3,5-triazin-2yl)-4-methylmorpholinium chloride); EDC or carbonyl diimidazole. Cleavage of the more labile anomeric protectant gives glycuronamide. See Scheme 1. Various protecting groups at the anomeric position of the molecule may be used as is well known in the art.

Scheme 1

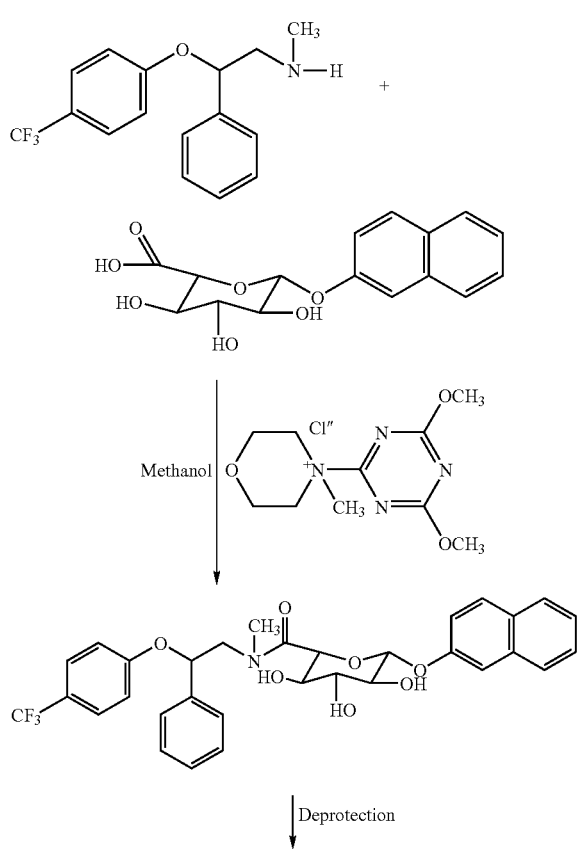

Deprotection

-continued

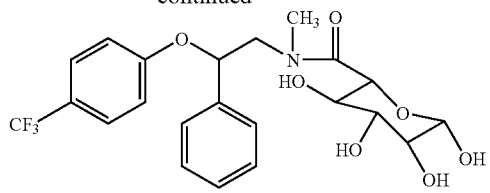

Representative examples of diseases and conditions treatable by compounds of the present invention are as listed hereinabove, and include, but are not limited to, depression, eating disorders, obsessive-compulsive disorder, bulimia, pain, obsessive-compulsive personality disorder, post-traumatic stress disorder, hypertension, atherosclerosis, anxiety, anorexia nervosa, panic, social phobia, stuttering, sleep disorders, chronic fatigue, Alzheimer's disease, alcohol abuse, appetite disorders, weight loss, agoraphobia, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of antidepressants, aggressive/intermittent explosive disorder, compulsive gambling, compulsive spending, compulsive sex, psychoactive substance use disorder, schizophrenia, premature ejaculation, or pyschiatric symptoms selected from the group consisting of stress, worry, anger, rejection sensitivity, and lack of mental or physical energy without an increase in nausea.

Particularly preferred routes of administration of the compounds of the present invention are per os, such as elixirs, tablets and capsules, as exemplified below.

More generally, the compounds of the present invention can be administered in any appropriate pharmaceutically acceptable carrier for oral administration since the fluoxetine and analog thereof-glycosides/orthoester glycosides/glycuronamides are biologically active upon oral administration. The compounds of the invention may also be administered in any appropriate pharmaceutical carrier for parenteral, intramuscular, transdermal, intranasal, buccal or inhalation administration. They can be administered by any means that treat or ameliorate the conditions and diseases described herein.

The dosage administered will depend on the age, health and weight of the recipient, kind of concurrent treatment, if any, frequency of treatment and the nature of the effect desired. An exemplary systemic daily dosage is about 0.1 mg to about 500 mg. Normally, from about 1.0 mg to 100 mg daily of the glycoside/orthoester glycoside/glycuronamide, in one or more dosages per day, is effective to obtain the desired results. One of ordinary skill in the art can determine the optimal dosages and concentrations of active compounds with only routine experimentation.

The compounds can be employed in dosage forms such as tablets and capsules for oral administration. Such dosage forms may comprise well know pharmaceutically acceptable carriers and excipients. In a preferred embodiment, the dosage forms comprise cyclodextran and/or other saccharides and/or sugar alcohols. The compounds may also be formulated in a sterile liquid for formulations such as solutions or suspensions for parenteral use. A lipid vehicle can be used in parenteral administration. The compounds could also be administered via topical patches, ointments, gels or other transdermal applications. In such compositions, the active ingredient will ordinarily be present in an amount of at least 0.001% by weight based on the total weight of the composition, and not more than 50% by weight. An inert pharmaceutically acceptable carrier is preferable such as 95% ethanol, vegetable oils, propylene glycols, saline buffers, sesame oil, etc. *Remington's Pharmaceutical Sciences*, 18$^{th}$ Edition, Gennaro et al. (eds.), 1990, exemplifies methods of preparing pharmaceutical compositions.

The compounds may also be employed in fast dissolving dosage forms, as described in U.S. Pat. No. 6,316,027, comprising the compounds of the invention, water, gelatin and other ingredients.

Topical formulations for transdermal, intranasal or inhalation administration may be prepared according to methods well known in the art. For topical administration, the compounds may be applied in any of the conventional pharmaceutical forms. For example, the compounds may be administered as part of a cream, lotion, aerosol, ointment, powder, drops or transdermal patch. Ointments and creams may, for example, be formulated with an aqueous or oily base with the addition of suitable thickening and/or gelling agents. Such bases may include water and/or an oil such as liquid paraffin or a vegetable oil such as peanut oil or castor oil. Thickening agents which may be used include soft paraffin, aluminum stearate, cetostearyl alcohol, polyethylene glycols, wool-fat, hydrogenated lanolin, beeswax and the like.

Lotions may be formulated with an aqueous or oily base and will in general also include one or more of a stabilizing agent, thickening agent, dispersing agent, suspending agent, thickening agent, coloring agent, perfumre and the like.

Powders may comprise any suitable powder base including talc, lactose, starch and the like. Drops may comprise an aqueous or non-aqueous base together with one or more dispersing agents, suspending agents, solubilizing agents and the like.

The compositions may further comprise one or more preservatives including bacteriostatic agents including methyl hydroxybenzoate, propyl hydroxybenzoate, chlorocresol, benzalkonium chloride and the like.

The topical compositions comprise from about 0.0001% to 5% by weight, preferably, 0.001 to 0.5% by weight, more preferably, 0.01 to 0.25% by weight of the active compounds.

The compounds of the invention are substantially pure. The phrase "substantially pure" encompasses compounds created by chemical synthesis and/or compounds substantially free of chemicals which may accompany the compounds in the natural state, as evidenced by thin layer chromatography (TLC) or high performance liquid chromatography (HPLC). Such "substantially pure" compounds do not include, for example, lactosyl fluoxetine which may be present in dosages forms comprising fluoxetine hydrochloride and lactose.

Animals which may be treated according to the methods of the present invention include all animals which may benefit therefrom. Included in such animals are humans, although the invention is not intended to be so limited.

Having now generally described this invention, the same will be understood by reference to the following examples which are provided herein for purposes of illustration only and are not intended to be limiting unless otherwise specified.

EXAMPLE 1

Synthesis of (±)-N-Methyl-3-phenyl-3{(α-α-α-trifluoro-p-tolyl)oxy}-propylamine

N-(α' & β'-glucopyranosyl)-(±)-N-Methyl-3-phenyl-3 {(α-α-α-trifluoro-p-tolyl)oxy}propylamine (fluoxetine-N-glcoside) was synthesized according to the following method set forth in Scheme 2.

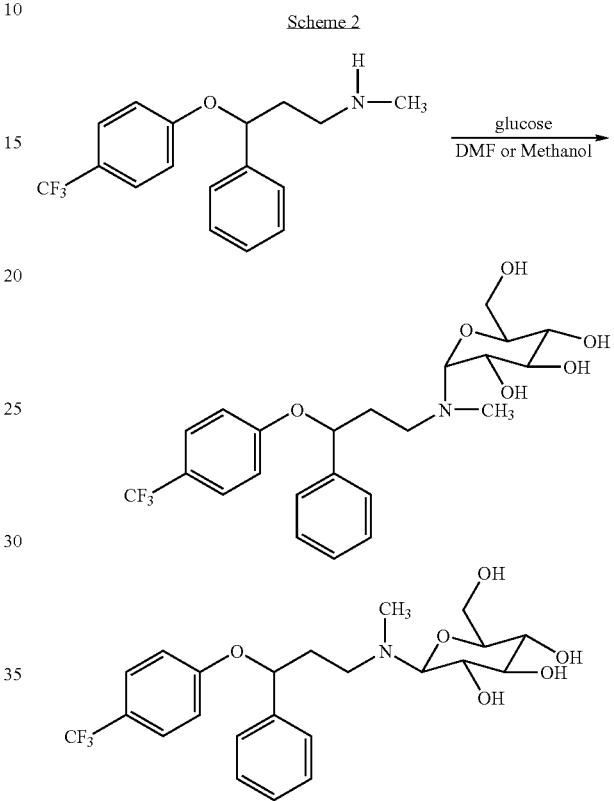

Scheme 2

(±)-N-Methyl-3-phenyl-3{(α-α-α-trifluoro-p-tolyl) oxy}propylamine (fluoxetine) was purchased from Sigma as the hydrochloride.

(±)-N-Methyl-3-phenyl-3{(α-α-α-trifluoro-p-tolyl) oxy}propylamine hydrochloride (fluoxetine hydrochloride; 100 mg) was suspended in deionized water (5 ml) and cooled to 4° C. A solution of sodium hydroxide (1 mg/ml; 10 ml) was added and the solution was stirred for 30 minutes at 4° C. The mixture was allowed to warm to room temperature and extracted with dichloromethane (3×25 ml). The organic layer was washed once with water (5 ml) and dried over anhydrous magnesium sulfate. Dichloromethane was evaporated under reduced pressure to give oil in quantitative manner. This oil was used without any further purification.

EXAMPLE 2

Synthesis of N-(α'& β'-glucopyranosyl)-(±)-N-Methyl-3-phenyl-3{(α-α-α-trifluoro-p-tolyl) oxy}propylamine (fluoxetine-N-glucoside)

Fluoxetine or (±)-N-Methyl-3-phenyl-3{(α-α-α-trifluoro-p-tolyl)oxy}propylamine (90 mg from above) was dissolved in dry N,N-dimethyl formamide (5 ml) and α-D-glucose (60 mg) was added. The mixture was stirred under argon atmosphere and shaken at 37° C. for about 5 hours during which time most of the glucose dissolved to afford a clear solution. The solution was cooled to room temperature and centrifuged to remove any excess glucose. The solvent was lyophilized off to afford a viscous paste (148 mg) in a quantitative manner. The product was characterized to be a mixture of α & β-anomeric forms of fluoxetine-N-glucoside.

The proton NMR spectrum of N-(α'& α'-glucopyranosyl)-(±)-N-Methyl-3-phenyl-3{(α-α-α-(trifluoro-p-tolyl)oxy}propylamine (fluoxetine-N-glucoside) in CD₃OD:
δ 6.8–7.4 (multiplets, Aryl-H, 9H); 5.5 (broad singlet, O—CH-benzyl, 1H); 5.1 (singlet, anomeric-α-H, 45% ratio); 4.4 (d, 7.8 Hz, anomeric-β-H, 55% ratio); 2.6–3.8 (multiplets, sugar-H & N—CH₂, 8H); 2.3 (two closely overlapping singlets, N—CH₃, 3H) and 1.9–2.2 (two broad multiplets, aliphatic-H, 2H).

Mass spectrum of the mixture as a Na⁺ adduct showed molecular weight of 494.3 amu consistent with the structure.

EXAMPLE 3

Synthesis of N-(α' & β'-glucopyranosyl)-(±)-N-Methyl-3-phenyl-3{(α-α-α-trifluoro-p-tolyl)oxy}propylamine (fluoxetine-N-glucoside)

Fluoxetine (90 mg) was dissolved in methanol (5 ml) and and α-D-glucose (60 mg) was added. The mixture was shaken at 45° C. for 12 hours under argon and all of the glucose dissolved during this time. The mixture was cooled to room temperature filtered off. Upon evaporating the solvent at reduced pressure gave the N-glucoside (132 mg) as a mixture of α & β anomeric forms.

The proton NMR spectrum of N-(α' & β'-glucopyranosyl)-(±)-N-Methyl-3-phenyl-3{(α-α-α-trifluoro-p-tolyl)oxy}propylanine (fluoxetine-N-glucoside) in CD₃OD:
δ 6.8–7.4 (multiplets, Aryl-H, 9H); 5.5 (broad singlet, O—CH-benzyl, 1H); 5.1 (singlet, anomeric-α-H, 55% ratio); 4.4 (d, 7.8 Hz, anomeric-β-H, 45% ratio); 2.6–3.8 (multiplets, sugar-H & N—CH₂, 8H); 2.3 (two closely overlapping singlets, N—CH₃, 3H) and 1.9–2.2 (two broad multiplets, aliphatic-H, 2H).

Mass spectrum of the mixture as a Na⁺ adduct showed molecular weight of 494.3 amu consistent with the structure.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. A compound which is a glycuronamide of fluoxetine, or orthoester gylcoside of fluoxetine, or salt thereof.

2. The compound of claim 1, wherein the glycuronamide or orthoester glycoside has the Formula (I):

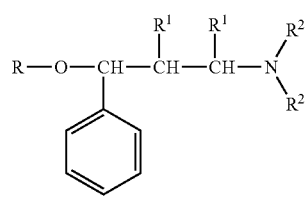

wherein each $R^1$ is independently hydrogen or methyl;
wherein one $R^2$ is methyl and the other $R^2$ is a glycuronamide or ortho ester glycoside;

wherein R is naphthyl or

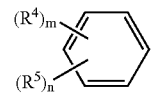

wherein $R^4$ and $R^5$ are halo, trifluoromethyl, $C_1$–$C_4$ alkyl, $C_1$–$C_3$ alkoxy or $C_3$–$C_4$ alkenyl; and
wherein n and m are 0, 1 or 2; and acid addition salts thereof formed with pharmaceutically-acceptable acids.

3. The compound of claim 2, wherein $R^2$ is an orthoester glycoside moiety of the Formula (II):

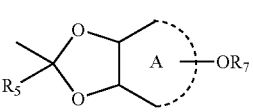

wherein A represents a glycofuranosyl or glycopyranosyl ring;
$R^6$ is hydrogen;
$R^7$ is hydrogen or a straight or branched chain glycosidic residue containing 1–20 glycosidic units per residue.

4. The compound of claim 1, having the Formula (III):

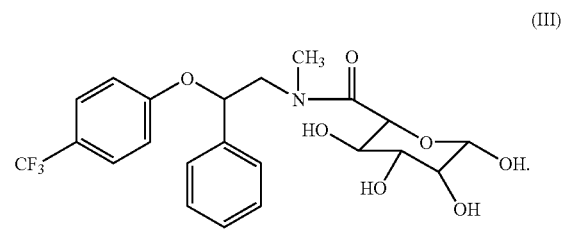

or a salt thereof.

5. The compound of claim 1, wherein said compound is a glucuronamide of fluoxetine.

6. A pharmaceutical composition comprising the compound of claim 1 and a pharmaceutically acceptable carrier.

7. A method for the treatment or amelioration of depression, comprising administering to an animal in need thereof an effective amount of the compound of claim 1.

8. The method of claim 7, wherein said compound is administered as part of a pharmaceutical composition comprising a pharmaceutically acceptable carrier therefor.

9. The method of claim 7, wherein said animal is a human.

10. The method of claim 7, wherein said compound has the Formula (III):

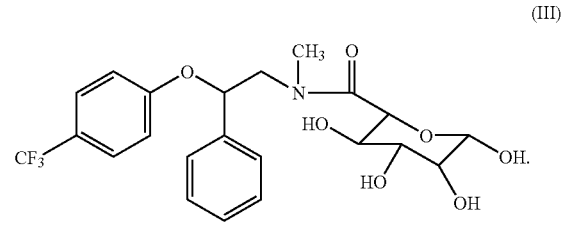

* * * * *